(12) United States Patent
Jagusch et al.

(10) Patent No.: US 11,434,243 B2
(45) Date of Patent: Sep. 6, 2022

(54) TRIAZOLOQUINAZOLINONE SYNTHESIS

(71) Applicant: GABATHER AB, Sodertalje (SE)

(72) Inventors: Thomas Jagusch, Bedburg-Hau (DE); Peter Adrianus Hubertus Zenhorst, PC Vught (NL); Paula Anna Adriana Van Der Aa, BC Nederasselt (NL); Govert Arie Verspui, CB Druten (NL); Martin Kas, Prague (CZ); Martina Scigelova, Cesky brod (CZ)

(73) Assignee: GABATHER AB, Sodertalje (SE)

( * ) Notice: Subject to any disclaimer, the term of this patent is extended or adjusted under 35 U.S.C. 154(b) by 0 days.

(21) Appl. No.: 16/954,795

(22) PCT Filed: Dec. 19, 2018

(86) PCT No.: PCT/IB2018/001573

§ 371 (c)(1),
(2) Date: Jun. 17, 2020

(87) PCT Pub. No.: WO2019/123011

PCT Pub. Date: Jun. 27, 2019

(65) Prior Publication Data

US 2021/0087193 A1      Mar. 25, 2021

Related U.S. Application Data

(60) Provisional application No. 62/607,353, filed on Dec. 19, 2017.

(51) Int. Cl.
   *C07D 487/06*      (2006.01)
   *C07D 487/04*      (2006.01)
(52) U.S. Cl.
   CPC .................. *C07D 487/04* (2013.01)
(58) Field of Classification Search
   CPC ................................................. C07D 487/06
   USPC ...................................................... 544/252
   See application file for complete search history.

(56) References Cited

FOREIGN PATENT DOCUMENTS

WO      2009/123537 A1      10/2009

OTHER PUBLICATIONS

International Search Report and Written Opinion in International Application No. PCT/IB2018/001573, dated Mar. 27, 2019.
Guerrini et al., "Pyrazolo[1,5-a]quinazoline scaffold as 5-deaza analogue of pyrazolo[5,1-c][1,2,4]benzotriazine system:synthesis of new derivatives, biological activity on GABAA receptor subtype and molecular dynamic study", J. Enzyme Inhib. Med. Chem., 2016, 31(2): 195-204.
Nilsson et al., "Triaologquinazolinediones as novel high affinity ligands for the benzodiazepine site of GABBA receptors", Bioorganic & Medicinal Chemistry, 2011, 19; 111-121.

*Primary Examiner* — Douglas M Willis
(74) *Attorney, Agent, or Firm* — J.A. Lindeman & Co., PLLC

(57) ABSTRACT

The invention relates to an improved process for preparing triazoloquinazolinones of Formula (I),

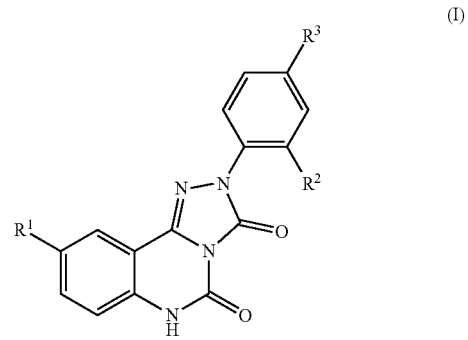

including 9-benzyl-2-(4-methylphenyl)-2,6-dihydro[1,2,4]triazolo[4,3-c]quinazoline-3,5-dione, pharmaceutical compositions comprising the compounds of Formula (I), including 9-benzyl-2-(4-methylphenyl)-2,6-dihydro[1,2,4]triazolo[4,3-c]quinazoline-3,5-dione, prepared by the improved process, and methods of treatment using the compounds of Formula (I), including 9-benzyl-2-(4-methylphenyl)-2,6-dihydro[1,2,4]triazolo[4,3-c]quinazoline-3,5-dione, prepared by the improved process.

3 Claims, No Drawings

TRIAZOLOQUINAZOLINONE SYNTHESIS

CROSS-REFERENCE TO RELATED APPLICATIONS

This application claims priority to U.S. application 62/607,353 filed Dec. 19, 2017, which is incorporated herein by reference.

FIELD OF THE INVENTION

The invention relates to the preparation of triazoloquinazolinones, compounds which have strong benzodiazepine receptor affinity.

BACKGROUND OF THE INVENTION

The γ-aminobutyric acid$_A$ (GABA$_A$) receptor complex is a pentameric assembly of several different protein subunits, which exist in multiple isoforms ($\alpha_{1-6}$, $\beta_{1-4}$, $\gamma_{1-4}$, θ, π, ε, $\rho_{1-3}$ and δ). (Whiting, P J et al. "Molecular and functional diversity of the expanding GABAA receptor gene family" Annals of the NY Academy of Sciences 1999, April 30, pp 645-653.) The most abundant of these GABA$_A$ receptors contain two α, two β and one γ subunits. Several ligands are known to allosterically modulate the GABA$_A$ receptor, such as benzodiazepine (BZD), barbiturates, ethanol and certain steroids. Historically, BZD has attracted most attention and has as such been used clinically for treatment as anxiolytic, anticonvulsant, muscle relaxant, and sedative-hypnotic drugs. (Nutt, D J and Malizia, A L "New insights into the role of GABA$_A$ receptors in psychiatric disorders", Br. J. Psychiatry (2001), Vol. 179, pp 390-396.

Receptors with different subtype composition are associated with different physiological effects, e.g., $\alpha_1$-containing receptors mediate sedation and anterograde amnesia, $\alpha_2$-, and/or $\alpha_3$-containing receptors are involved in anxiolytic activity, and $\alpha_5$-containing receptors might be associated with cognition and memory. (Whiting, P J "GABAA receptor subtypes in the brain: a paradigm for CNS drug discovery", Drug Discovery Today, Vol. 8, No. 10, May 2003, pp 445-450.) The $\alpha_1\beta_x\gamma_2$, $\alpha_2\beta_x\gamma_2$, $\alpha_3\beta_x\gamma_2$ and $\alpha_5\beta_x\gamma_2$ subtype assemblies are regard as the major benzodiazepine binding receptors, the benzodiazepine binding-site being located at the interface between the α and the γ subunit. BDZ receptor ligands are structurally different compounds, which bind to the (GABA$_A$)/BDZ receptor complex. They display a broad pharmacological effect stretching from the full agonistic agents exhibiting anxiolytic, anticonvulsant, sedative-hypnotic and myorelaxant activities to the inverse agonistic agents, which displays anxiogenic, and pro-convulsant activities. In between, antagonistic agents that elicit no pharmacological effect are present.

Side effects characteristically produced by benzodiazepines include: sedation, muscle relaxation, drug interaction effects, and dependence. (Bennett, DA "Pharmacology of the pyrazolo-type compounds: agonist, antagonist and inverse agonist actions", *Physiology & Behavior* (1987) Vol. 41, pp. 241-245.) Among the wide variety of nonbenzodiazepine ligands, the most potent and perhaps best studied belong to the following classes: 2-arylpyrazoloquinolines, β-carbolines, pyridodiindoles, pyrimidin-5(6H)-ones, triazoloqunioxalines, cyclopyrrolones, and quinolines. U.S. Pat. No. 8,809,355.

One triazoloquinazolinone, the compound 9-benzyl-2-(4-methylphenyl)-2,6-dihydro[1,2,4]triazolo[4,3-c]quinazoline-3,5-dione (compound 12, shown below), is a very potent inhibitor of the binding of $^3$H-Flumazenil binding to the benzodiazepine site of the GABA$_A$ receptor complex in rat membrane preparations. Compound 12 is 10 times more potent than diazepam in displacing $^3$H-Flumazenil and is selective for the GABA$_A$ receptor complex.

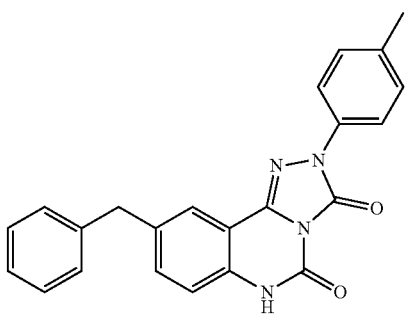

12

The preparation of compound 12 is described in Example 16a of U.S. Pat. No. 8,809,355, but this synthesis is not suitable for commercial production. The preparation utilizes benzyltributyltin reagent which can results in tin residues and was purified by chromatography on a silica gel column. The purification of compound 12 is complicated by its low solubility. There is a need therefore for an improved route to triazoloquinazolinones, such as compound 12, which avoids tin reagents and allows for uncomplicated purification.

SUMMARY OF THE INVENTION

The invention relates to an improved process for the preparation of compound of Formula (I) and its pharmaceutically acceptable salts:

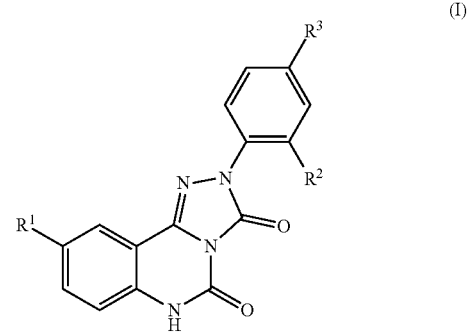

(I)

wherein $R^1$, $R^2$, and $R^3$ are defined herein. The invention further relates to compounds of Formula (I) or a pharmaceutically acceptable salt thereof prepared by the process of the invention.

In particular, the invention relates to an improved process for the preparation of 9-benzyl-2-(4-methylphenyl)-2,6-dihydro[1,2,4]triazolo[4,3-c]quinazoline-3,5-dione (compound 12):

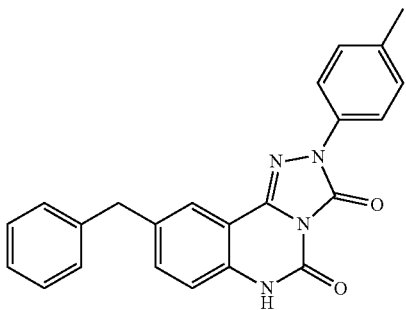

12

The invention is also directed to 9-benzyl-2-(4-methylphenyl)-2,6-dihydro[1,2,4]triazolo[4,3-c]quinazoline-3,5-dione prepared by the process of the invention.

The invention further relates to pharmaceutical compositions comprising a compound of Formula (I), including 9-benzyl-2-(4-methylphenyl)-2,6-dihydro[1,2,4]triazolo[4,3-c]quinazoline-3,5-dione, or a pharmaceutically acceptable salt thereof prepared by the process of the invention.

The invention also relates to methods of treating anxiolytic, anticonvulsant, sedative-hypnotic, myorelaxant, anxiogenic, somnolytic, and convulsant conditions in mammals by administering a therapeutically effective amount of at least one compound of Formula (I), including 9-benzyl-2-(4-methylphenyl)-2,6-dihydro[1,2,4]triazolo[4,3-c]quinazoline-3,5-dione, or a pharmaceutically acceptable salt thereof prepared by the process of the invention.

DESCRIPTION OF THE INVENTION

This invention relates to the production of triazoloquinazolinones of Formula (I) below, and pharmaceutically acceptable salts thereof, and in particular 9-benzyl-2-(4-methylphenyl)-2,6-dihydro[1,2,4]triazolo[4,3-c]quinazoline-3,5-dione (compound 12).

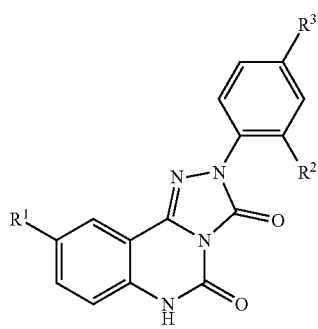

(I)

wherein:
$R^1$ is selected from the group consisting of halogen, alkyl having 1 to 2 carbon atoms, carboxyalkyl having 1 to 3 carbon atoms, phenyl-alkynyl- having 2 to 3 carbon atoms in the alkynyl chain, phenyl-alkenyl- having 1 to 3 carbon atoms in the alkenyl chain, phenyl-alkyl- having 1-3 carbon atoms in the alkyl chain and wherein the phenyl moiety may be further substituted by an oxygen or a sulphur atom in any position, pyridyl-alkyl- having 1 to 2 carbon atoms in the alkyl chain, and trifluoromethyl,
$R^2$ is selected from the group consisting of hydrogen and halogen, and
$R^3$ is selected from the group consisting of hydrogen, halogen, and alkyl having 1 to 2 carbon atoms.

Preferably, $R^1$ being halogen is selected from the group consisting of bromo, iodo, fluoro, and chloro.

Preferably, $R^1$ being alkyl is selected from the group consisting of methyl and ethyl.

Preferably, $R^1$ being carboxyalkyl is selected from the group consisting of carboxymethyl, carboxyethyl, and carboxypropyl.

Preferably, $R^1$ being phenylalkynyl is selected from the group consisting of phenylethynyl, phenyl-1-propynyl, and phenyl-2-propynyl.

Preferably, $R^1$ being phenylalkenyl is selected from the group consisting of phenylethenyl, phenyl-1-propenyl, and phenyl-2-propenyl.

Preferably, $R^1$ being phenylalkyl is selected from the group consisting of phenylmethyl, phenylethyl, phenylisopropyl, and phenylpropyl.

Preferably, $R^2$ being halogen is selected from the group consisting of bromo, iodo, fluoro, and chloro.

Preferably, $R^3$ being halogen is selected from the group consisting of bromo, iodo, fluoro, and chloro.

Preferably, $R^3$ being alkyl is selected from the group consisting of methyl, ethyl propyl, and isopropyl.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula (I) or any of its intermediates. Illustrative inorganic acids which form suitable salts include hydrochloric, hydrobromic, sulfuric, and phosphoric acid and acid metal salts such as sodium monohydrogen orthophosphate and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and other sulfonic acids such as methanesulfonic acid and 2-hydroxyethanesulfonic acid. Either the mono- or di-acid salts can be formed. In general, the acid addition salts of these compounds are more soluble in water and various hydrophilic organic solvents, and generally demonstrate higher melting points in comparison to their free base forms. One skilled in the art will know the selection criteria for the appropriate salt. Other non-pharmaceutically acceptable salts, e.g., oxalates, may be used for example in the isolation of compounds of Formula (I) for laboratory use, or for subsequent conversion to a pharmaceutically acceptable acid addition salt.

A "pharmaceutically acceptable basic addition salt" is any non-toxic organic or inorganic base addition salt of the acid compounds represented by Formula (I) or any of its intermediates. Illustrative inorganic bases which form suitable salts include lithium, sodium, potassium, calcium, magnesium, or barium hydroxides. Illustrative organic bases which form suitable salts include aliphatic, alicyclic, or aromatic organic amines such as methylamine, trimethyl amine and picoline or ammonia. The selection of the appropriate salt may be important so that an ester functionality, if any, elsewhere in the molecule is not hydrolyzed. One skilled in the art will know the selection criteria for the appropriate salt.

The term "stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereomers).

When compounds of the invention contain at least one chiral centers, the compounds of the invention may exist in, and be isolated as, enantiomeric or diastereomeric forms, or as a racemic mixture. The invention includes any possible enantiomers, diastereomers, racemates, or mixtures thereof, of a compound of Formula (I). The optically active forms of the compound of the invention may be prepared, for example, by chiral chromatographic separation of a racemate or chemical or enzymatic resolution methodology, by synthesis from optically active starting materials or by asymmetric synthesis based on the procedures described thereafter.

Certain compounds of the invention may exist as geometrical isomers, for example E and Z isomers of alkenes. The invention includes any geometrical isomer of a compound of Formula (I). The invention also encompasses tautomers of the compounds of Formula (I).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant, or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Triazoloquinazolinones of Formula (I), where $R^1$, $R^2$, and $R^3$ are as defined hereinabove, can be prepared using the process of the invention, as shown in Scheme 2. The process of the invention achieves large scales and is suitable for commercial production. Each step is described below.

Scheme 2

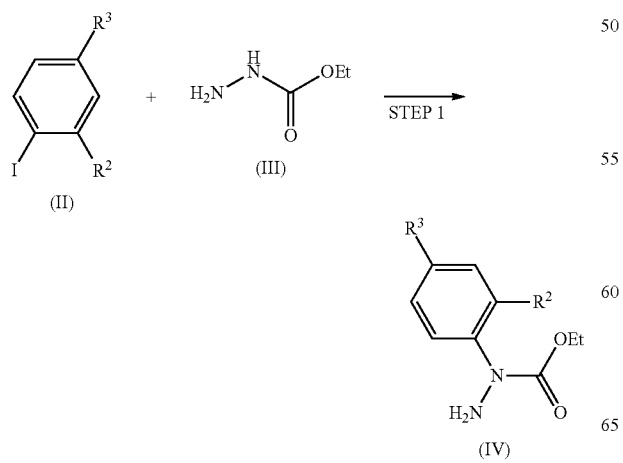

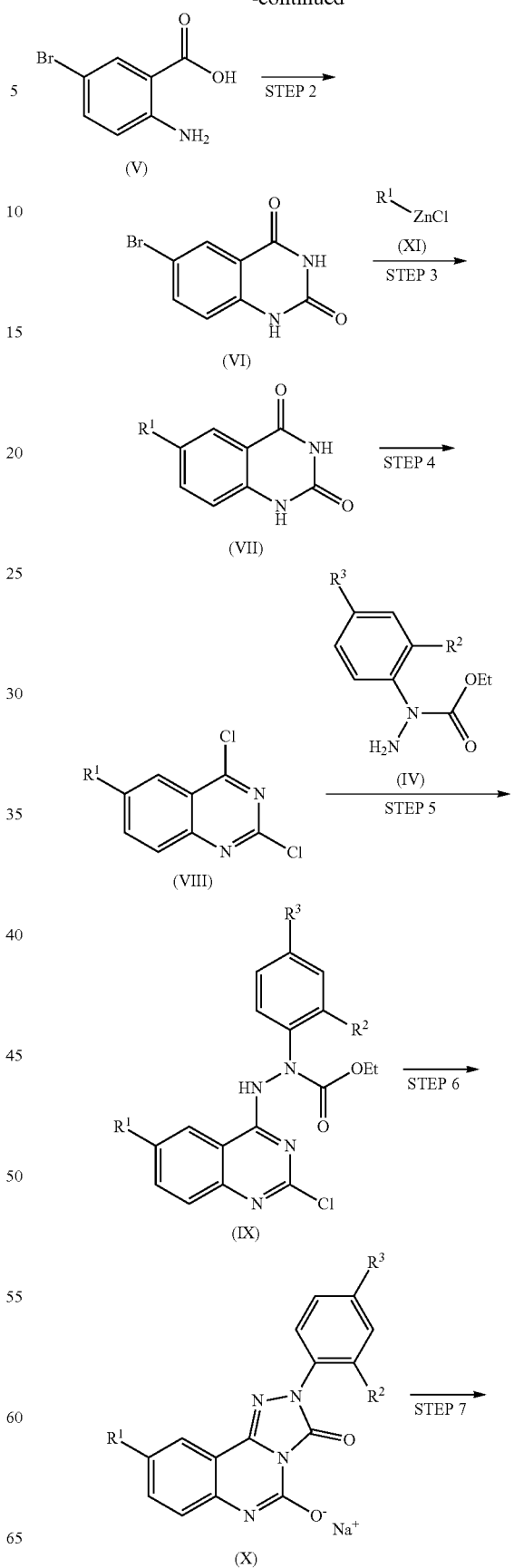

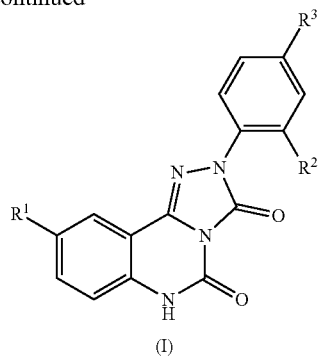

In Step 1, a compound of Formula (II) is reacted with a compound of Formula (III) under conditions sufficient to form a compound of Formula (IV). For example, a compound of Formula (IV) can be formed by charging an oxygen-free reactor with dimethylsulfoxide, a compound of Formula (III), cesium carbonate, a compound of Formula (II), and copper(I) iodide, preferably in that order, the reactor can be heated to form a crude compound of Formula (IV), the hydrochloride salt of compound of Formula (IV) can be worked-up by dissolving the crude material in toluene and adding hydrogen chloride (4M solution in dioxane), and the hydrochloride salt of compound of Formula (IV) can be purified and can form its free base by suspending it in ethyl acetate and adding sodium bicarbonate dissolved in water.

In Step 2, a compound of Formula (V) is reacted under conditions sufficient to form a compound of Formula (VI). For example, a compound of Formula (VI) can be formed by heating a compound of Formula (V), urea, and N-methyl-2-pyrrolidinone.

In Step 3, a compound of Formula (VI) is reacted with a zinc reagent of Formula (XI) under conditions sufficient to form a compound of Formula (VII). For example, a compound of Formula (VII) can be formed by a Negishi coupling of a compound of Formula (VI) and a zinc reagent of Formula (XI). A zinc reagent of Formula (XI) can be added to a reactor charged with a compound of Formula (VI), palladium(II) acetate, tri-tert-butylphosphonium tetrafluoroborate, and tetrahydrofuran.

A compound having the formula $R^1$—Cl can be reacted under conditions sufficient to form a zinc reagent of Formula (XI). For example, a zinc reagent of Formula (XI) can be formed by reacting a compound having the formula $R^1$—Cl with zinc powder in tetrahydrofuran and dimethyl sulfoxide.

In Step 4, a compound of Formula (VII) is reacted under conditions sufficient to form a compound of Formula (VIII). For example, a compound of Formula (VIII) can be formed by charging a reactor with a compound of Formula (VII) and acetonitrile, and adding phosphorous oxychloride and diisopropylethylamine.

In Step 5, a compound of Formula (VIII) is reacted with a compound of Formula (IV) under conditions sufficient to form a compound of Formula (IX). For example, a compound of Formula (IX) can be formed by refluxing a compound of Formula (IV) in 2-propanol with N,N-diisopropylethylamine.

In Step 6, a compound of Formula (IX) is reacted under conditions sufficient to form a compound of Formula (X). For example, a compound of Formula (X) can be formed by heating a mixture of a compound of Formula (IX) and 1,4-dioxane.

In Step 7, a compound of Formula (X) is reacted under conditions sufficient to form a compound of Formula (I). For example, a compound of Formula (I) can be formed by refluxing a compound of Formula (X) with acetic acid.

Using compound 12 as an example, the seven-step process of the invention is shown in Scheme 1. The process achieves large scales and is suitable for commercial production. Each step is described below.

Scheme 1

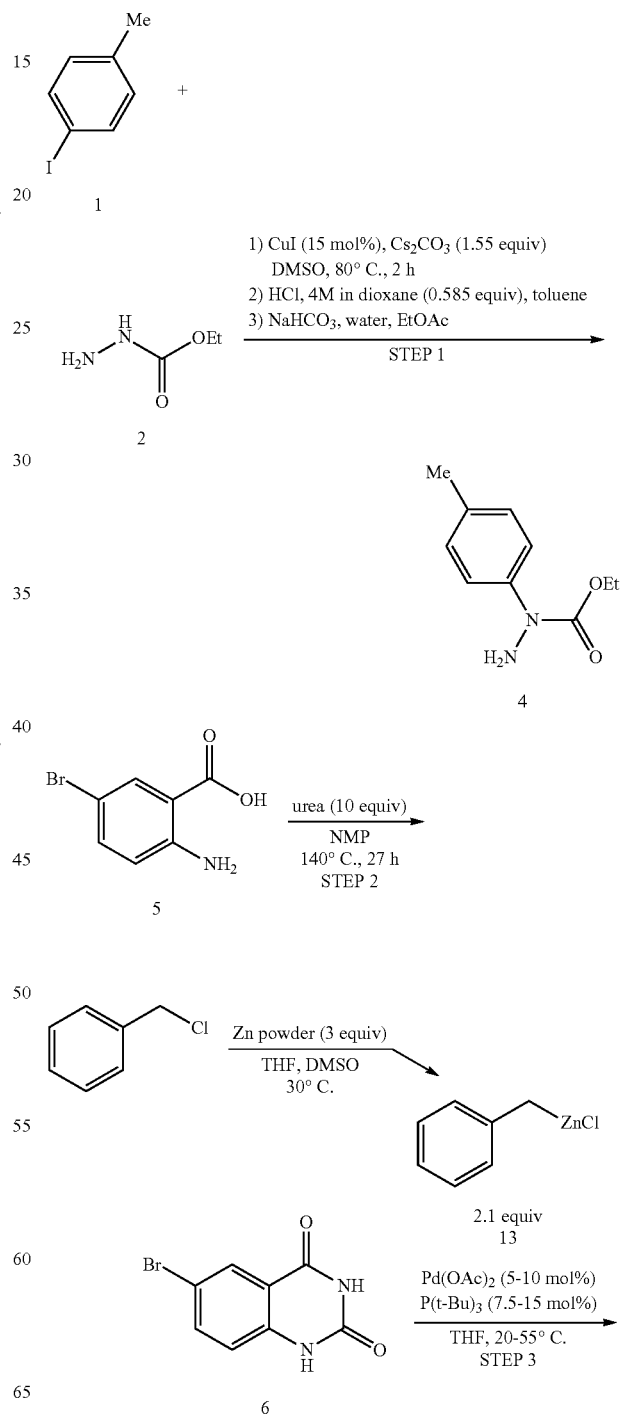

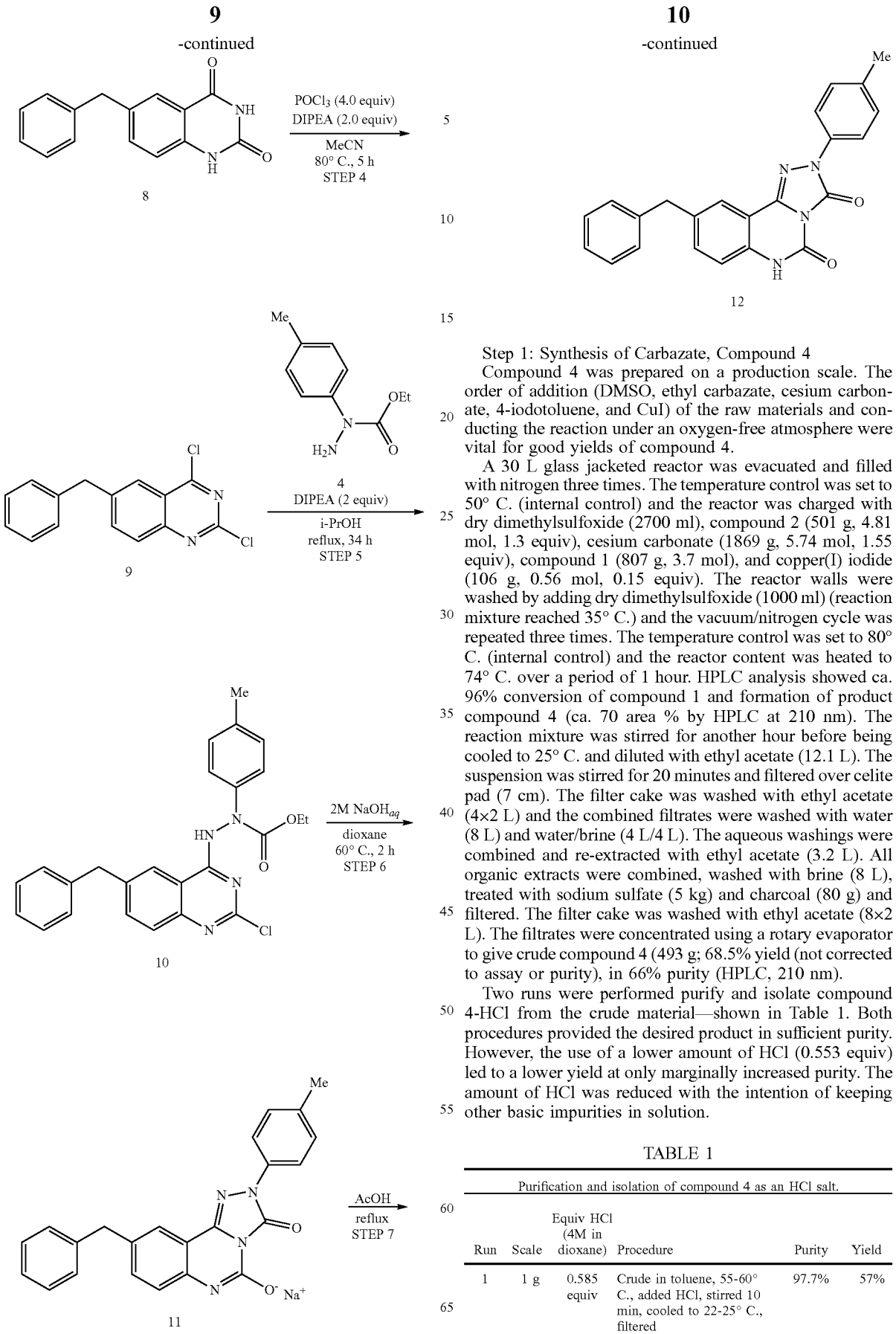

Step 1: Synthesis of Carbazate, Compound 4

Compound 4 was prepared on a production scale. The order of addition (DMSO, ethyl carbazate, cesium carbonate, 4-iodotoluene, and CuI) of the raw materials and conducting the reaction under an oxygen-free atmosphere were vital for good yields of compound 4.

A 30 L glass jacketed reactor was evacuated and filled with nitrogen three times. The temperature control was set to 50° C. (internal control) and the reactor was charged with dry dimethylsulfoxide (2700 ml), compound 2 (501 g, 4.81 mol, 1.3 equiv), cesium carbonate (1869 g, 5.74 mol, 1.55 equiv), compound 1 (807 g, 3.7 mol), and copper(I) iodide (106 g, 0.56 mol, 0.15 equiv). The reactor walls were washed by adding dry dimethylsulfoxide (1000 ml) (reaction mixture reached 35° C.) and the vacuum/nitrogen cycle was repeated three times. The temperature control was set to 80° C. (internal control) and the reactor content was heated to 74° C. over a period of 1 hour. HPLC analysis showed ca. 96% conversion of compound 1 and formation of product compound 4 (ca. 70 area % by HPLC at 210 nm). The reaction mixture was stirred for another hour before being cooled to 25° C. and diluted with ethyl acetate (12.1 L). The suspension was stirred for 20 minutes and filtered over celite pad (7 cm). The filter cake was washed with ethyl acetate (4×2 L) and the combined filtrates were washed with water (8 L) and water/brine (4 L/4 L). The aqueous washings were combined and re-extracted with ethyl acetate (3.2 L). All organic extracts were combined, washed with brine (8 L), treated with sodium sulfate (5 kg) and charcoal (80 g) and filtered. The filter cake was washed with ethyl acetate (8×2 L). The filtrates were concentrated using a rotary evaporator to give crude compound 4 (493 g; 68.5% yield (not corrected to assay or purity), in 66% purity (HPLC, 210 nm).

Two runs were performed purify and isolate compound 4-HCl from the crude material—shown in Table 1. Both procedures provided the desired product in sufficient purity. However, the use of a lower amount of HCl (0.553 equiv) led to a lower yield at only marginally increased purity. The amount of HCl was reduced with the intention of keeping other basic impurities in solution.

TABLE 1

Purification and isolation of compound 4 as an HCl salt.

| Run | Scale | Equiv HCl (4M in dioxane) | Procedure | Purity | Yield |
|---|---|---|---|---|---|
| 1 | 1 g | 0.585 equiv | Crude in toluene, 55-60° C., added HCl, stirred 10 min, cooled to 22-25° C., filtered | 97.7% | 57% |

TABLE 1-continued

Purification and isolation of compound 4 as an HCl salt.

| Run | Scale | Equiv HCl (4M in dioxane) | Procedure | Purity | Yield |
|-----|-------|---------------------------|-----------|--------|-------|
| 2 | 54 g | 0.553 equiv | Crude in toluene, 60° C., added HCl, stirred 10 min, cooled to 22-25° C., filtered | 98.2% | 49.5% |

Further work-ups isolated compound 4-HCl from the crude material using 0.585 equivalents hydrochloric acid. Compound 4 (432.8 g) was dissolved in toluene (4328 ml) at 22° C. The solution was heated to 59° C. over 40 minutes. Hydrogen chloride (4M solution in dioxane, 326 ml, 1304 mmol, 0.585 equiv) was added over a period of 10 minutes at 59-62° C. The product started to crystallize at 62° C. during the addition of hydrogen chloride. Upon complete addition, the reactor content was stirred at 62° C. for 5 minutes and then cooled down to 20° C. over a period of 2 hours. The suspension was stirred at 20° C. for 30 minutes filtered off and washed with toluene (3×800 ml), and dried on a rotary evaporator at 60° C. for 6 hours to give compound 4-HCl (291.6 g, 1264 mmol, 57% yield) as a slightly pinkish solid. The purity of the isolated product was 98.0%. The free base of the carbazate was prepared to circumvent problem with regioselectivity in step 5 (below).

Compound 4-HCl (353.1 g, 1531 mmol) were suspended in ethyl acetate (2500 ml) at 22° C. Sodium bicarbonate (257 g, 3061 mmol) was dissolved in water (2800 ml), and this solution was added at 23-16° C. to the suspension of Compound 4-HCl (endothermic reaction). The biphasic system was stirred at 22-25° C. over a period of 30 minutes. The phases were separated. The aqueous layer was washed with ethyl acetate (2×500 ml). The combined organic layers were dried over sodium sulfate (540 g, 1 hour) and filtered. The filtrate was concentrated and dried (1 hour at 40° C., 8 mbar) by rotary evaporation to afford the free base of compound 4 (269.2 g, 1386 mmol, 91% yield,) as a light brown oil. The purity was 97.5% (LCMS, DAD 210 nm).

Step 2: Quinazolindione Synthesis, Compound 6

A 30 L glass-jacketed reactor was charged with urea (2591 g, 43.14 mol, 10 equiv), compound 5 (932 g, 4.31 mmol), and N-methyl-2-pyrrolidinone (2800 ml). The suspension was heated to 140° C. and the resulting brown solution was stirred at 140-146° C. for a total time of 27 hours. After 6.5 hours, HPLC analysis showed 99% conversion of the starting material and formation of ureido-intermediate (30%) together with product compound 6 (65%). After 25.5 hours, product, compound 6, was present in the reaction mixture to an extent of 97.5% (HPLC). The reaction mixture was cooled to 90° C. and water (9320 ml) was added over a period of 1 hour while keeping the temperature of the reactor content at 82-92° C. The suspension was stirred at 88-92° C. for 1 hour and then was cooled to 20° C. over a period of 105 minutes. The product was filtered off, the filter cake was washed with water (3×2500 ml) and dried at 105° C. for 15 hours to give 953 g (92% yield) of beige product with a purity>99.5%.

Step 3: Benzyl Zinc Reagent Preparation and Negishi Coupling

Benzyl reagent preparation 1: To prepare the benzyl zinc reagent, compound 13, a 6 L flask equipped with magnetic stirring bar was charged with dry tetrahydrofuran (850 ml) and zinc powder (775 g, 11.85 mol, 3 equiv, Fluka 00618) while stirring under nitrogen. Benzyl chloride (500 g, 3.95 mol) was dissolved in dry tetrahydrofuran (3100 ml) and this solution was further diluted with dry dimethyl sulfoxide (850 ml). The solution of benzyl chloride was added to the zinc suspension at 25° C. over a period of 30 minutes. An exothermic reaction was not observed. The temperature of the organo zinc slurry was increased to 30-33° C. and stirring was continued for another 19 h. The heating was switched off and the suspension was stirred at 25° C. for 3.5 days. The stirring was switched off and the unreacted zinc was allowed to settle to bottom and a cloudy solution of benzyl zinc chloride, BnZnCl, was decanted. In this way, a benzyl zinc chloride ca 0.7 M solution (4850 g, 4942 ml, d 0.9814 g/ml, 3.459 mol, 88% yield,) was prepared.

Benzyl reagent preparation 2: Benzyl zinc chloride, compound 13, solution was manufactured in the same way but with the difference that the temperature was increased to 30-33° C. right after the addition of benzyl chloride. The stirring was switched off and the unreacted zinc was allowed to settle, and a cloudy solution of benzyl zinc chloride was decanted. Benzyl zinc chloride, BnZnCl, ca. 0.7 M solution (4980 g, 5074 ml, d 0.9814 g/ml, 3.552 mol, 90% yield,) was thus obtained.

Negishi coupling 1: A Negishi coupling was conducted on a 300 g scale using the first benzylzinc chloride solution preparation 1. A 10 L double jacketed glass reactor was charged with compound 6 (300 g, 1245 mmol), palladium (II) acetate (27.9 g, 124 mmol, 10 mol %), tri-tert-butylphosphonium tetrafluoroborate (54.2 g, 187 mmol, 15 mol %) and dry tetrahydrofuran (1950 ml). The reactor containing the suspension was partially evacuated (to 150 mbar) and filled with nitrogen three times. The benzyl zinc chloride, compound 13, solution (ca 0.7M) (3566 ml, ~2496 mmol, ~2.0 equiv, greyish turbid liquid) was added at 22-31° C. (exothermic) over a period of 29 minutes via a dropping funnel under nitrogen with active cooling of the reactor jacket (0° C.). Upon complete addition, the jacket set-point temperature was changed to 30° C. After 90 minutes a sample was taken and HPLC analysis (10 µl sample diluted with acetonitrile, 2 ml; water, 1 ml; and dimethylacetamide, 10 µl; then filtered through a PTFE 0.45 µm syringe filter) showed 2.53% remaining starting material. Another portion of BnZnCl solution (ca 0.7M) (106 ml, ~74.2 mmol, 0.06 equiv) was added, the temperature control was switched to reactor (external) and set to 55° C. A sample was taken after 35 minutes which showed 1.70% of remaining starting material. A third portion of benzylzinc(II) chloride (ca 0.7M, preparation 1) (97.8 ml, ~68.5 mmol, ~0.055 equiv) was added at once and the conversion reached 98.95% within 15 minutes after addition.

The reaction mixture was cooled to 23° C. over a period of 30 minutes. While cooling further (set point −5° C.), hydrochloric acid (1 M, 5153 ml, 5153 mmol) was added at 15-24° C. over a period of 32 minutes. The temperature of the jacket was set to 20° C., and the reaction was post stirred for 45 minutes. The jacket temperature was set to −5° C. and the suspension was cooled to 10° C. over a period of 23 minutes. The jacket temperature was set to 10° C. and the suspension was filtered (sintered glass filter S3). The filtration took 1 hour. The grey muddy filter cake was mixed with water (2 L) and sucked dry three times. The wet product (834 g) was dried on rotary evaporator (8 hours, 90° C., 12 mbar) to give compound 8 (317.4 g, 1258 mmol, 101% yield, batch MAKA08-027) in a purity of 95.68%. It was found that the impurity eluting at 5.356 minutes was volatile and can be removed completely by prolonged drying. This was demonstrated with a small sample in which case the overall impurity improved to ca 97%.

Negishi coupling 2: A second Negishi coupling was performed on a 300 g scale using ca ½ of standard pre-catalysts loading but more of the benzyl zinc chloride, compound 13, solution from preparation 2 (4074 g vs 3698 g in Negishi 1). A 10 L double jacketed glass reactor was charged with compound 6 (300 g, 1245 mmol), palladium (II) acetate (15.00 g, 66.8 mmol, 5.37 mol %), tri-tert-butylphosphonium tetrafluoroborate (29.1 g, 100 mmol, 8.05 mol %) and dry tetrahydrofuran (1950 ml). The reactor containing the suspension was partially evacuated (to 150 mbar) and filled with nitrogen three times. The benzyl zinc chloride solution (ca 0.7M, preparation 2) (3825 ml, ~2678 mmol, ~2.15 equiv, greyish turbid liquid) was added at 25-35° C. over a period of 30 minutes via a dropping funnel under nitrogen with active cooling of the reactor jacket (0° C.). Upon complete addition, the jacket set-point temperature was changed to 30° C. After 60 minutes a sample was taken and HPLC analysis showed 1.15% remaining starting material. Another portion of BnZnCl solution (ca 0.7M) (326 ml, ~228 mmol, 0.18 equiv) was added over a period of 5 minutes, the temperature control was switched to reactor (external) and set to 55° C. The reaction mixture was stirred at 50-55° C. for 50 minutes. HPLC analysis of the reaction mixture sample showed less than 0.3% of remaining starting material.

The reaction mixture was cooled to 20° C. over a period of 70 minutes. While cooling further (set point −5° C.), hydrochloric acid (1 M, 5153 ml, 5153 mmol) was added at 15-24° C. over a period of 30 minutes. The temperature of the jacket was set to 20° C., and the reaction was post stirred for 48 minutes. The jacket temperature was set to −5° C. and the suspension was cooled to 10° C. over a period of 27 minutes. The jacket temperature was set to 10° C. and the suspension filtered (sintered glass filter S3). The filtration took 30 minutes. The grey muddy filter cake was mixed with water (2 L) and sucked dry three times. The wet product was dried on rotary evaporator (8 hours, 90° C., 12 mbar) to give compound 8 (295.2 g, 1170 mmol, 94% yield).

Step 4: Chlorination

A 10 L double jacketed glass reactor was charged with acetonitrile (3030 ml, anhydrous) and compound 8 (638 g, 2529 mmol) under a nitrogen atmosphere. The suspension was cooled to 10° C. over a period of 10 minutes and phosphorus oxychloride (943 ml, 10.1 mol, 4.0 equiv) was added via funnel over a period of 2 minutes. The jacket set-point temperature was changed to 0° C. Diisopropylethylamine (969 ml, 5564 mmol, 2.20 equiv) was added via funnel over a period of 12 minutes. The temperature of the reaction mixture rose to 30° C. and evolution of white smoke was visible during the addition. The resulting black solution was subsequently heated to 80° C. and stirred at 80-84° C. for 6 hours. HPLC analysis after 5 hours showed 1% remaining starting material. The mixture was cooled to 20° C. and left without stirring overnight.

Acetonitrile and POCl$_3$ were distilled off using a rotary evaporator (water bath 50-90° C., pressure: 250-10 mbar), and the black, liquid residue was co-evaporated with 1.0 L of dry toluene (oil bath 120-155° C.) (83-109° C., 750 ml). The residue was cooled down to room temperature (22° C.). The mixture was left without stirring over a weekend at 22° C. The residue was further concentrated on a rotary evaporator (100-150° C. oil bath, 200-8 mbar) to give a distillate (250 ml) and a residue (2114 g). This residue was dissolved in ethyl acetate (6380 ml).

For convenience of handling, this solution was split into two equal parts, and each part was poured into a vigorously stirred aqueous 2 M solution of dibasic potassium phosphate (4426 ml, 8852 mmol) at 5-10° C. The biphasic mixture was stirred and warmed to 18° C. over a period of 30 minutes before the phases were separated. The organic layer contained wet, voluminous, insoluble matter. The organic layers of both parts were united, and a drying agent (MgSO$_4$, 2182 g) was added in several portions under cooling at 14-28° C. over a period of 30 minutes. Filtration and removal of the volatiles on a rotary evaporator (8 hours at 60° C.) furnished compound 9 (746.1 g, 2580 mmol, 102% of theory) as soft brown chunks/pellets. The material was stored in a closed flask under ambient atmosphere.

The prepared batch of compound 9 exhibited a lower purity (95.95%, HPLC) than desired. The observed deterioration of the purity might have been due to prolonged contact with atmospheric humidity during the work-up procedure. A use test of compound 9 was performed involving the follow-up steps 5 and 6. This reaction sequence afforded compound 11 in a HPLC purity of >97%.

Step 5: Addition of Carbazate

A solution of free base compound 4 (254 g, 1310 mmol) in 2-propanol (3787 ml) was treated with N,N-diisopropylethylamine (456 ml, 2619 mmol, 2 equiv) at room temperature.

The yellow solution was heated to reflux (water bath 85° C.), and stirred under reflux for a total time of 34 hours. The mixture was cooled down to 25° C., passed through a sintered glass filter (S3), concentrated on a rotary evaporator (250-120 mbar, water bath 30-50° C.) and dried at 70° C. for 2 hours, to give 810 g of a brown oil (138% of theory). This material was used as is the next step.

Step 6: Ring Closure to Triazolone, Compound 11

Half of the prepared crude compound 10 from Step 5 was used. A 6 L flask was charged with solution of ethyl 2-(6-benzyl-2-chloroquinazolin-4-yl)-1-(p-tolyl)hydrazine-1-carboxylate (293 g, 655 mmol, calculated as ½ of 100% theoretical yield of previous step MAKA08-035) dissolved in 1,4-dioxane (4300 ml). The resulting dark brown solution was heated to 60° C. on a water bath (64° C.). An aqueous 2 M solution of sodium hydroxide (1601 ml, 3203 mmol) was added in one portion (temperature drop to 45° C.). The reaction mixture was stirred at 55-60° C. for 90 minutes.

Within 10 minutes, solids began to precipitate. HPLC analysis showed no starting material to be left in the reaction mixture. The mixture was cooled down to 23° C. over a period of 50 minutes period and was post stirred at this temperature for 35 minutes. The beige suspension was filtered off and the filter cake was washed with dioxane/water 1:1 (4×500 mL). The beige filter cake was dried by rotary evaporation over 3 hours at 50° C. to arrive at crude compound 11 (202 g, 76% yield, 82.57% purity) as a beige solid.

The second half of prepared crude compound 10 was processed in the same manner to give compound 11 (217 g, 82% yield, 81.59% purity) as a beige solid. Both batches contained significant levels of an impurity IMP at 24.3 min. This impurity had a very, very low solubility in common solvents.

Step 7: Synthesis of Compound 12

The two batches of intermediate compound 11 were combined and treated with acetic acid to prepare the final product compound 12 and to simultaneously perform the final crystallization step. A 20 L reaction vessel was charged with compound 11 (413.5 g, 1022 mmol) and 16 L acetic acid. The suspension was heated to 110° C. (jacket temperature: 145° C.), 41 g charcoal was added and the suspension was stirred at 120-124° C. for 1 hour. The temperature was lowered to 95° C. and then the mixture was filtered (Accugaf polypropylene filter, porosity 1 µm). The reaction vessel was rinsed with 5 L acetic acid at 95° C. and the resulting washing liquid was filtered on the same filter.

The combined hot filtrates were transferred to a second 30 L reactor in which a spontaneous precipitation occurred. The first vessel and filter were washed with additional acetic acid (1.7 L), which was also added to the second reactor and the mixture was heated to 105° C. to give a clear yellowish solution. The temperature was slowly decreased overnight to 22° C. while gently stirring. The resulting suspension was passed through a sintered glass filter, the filter cake was washed with acetic acid (500 ml) and subsequently with water (3×1 L). The white product (filter cake) was dried in a rotary evaporator at 60° C. for 6 hours to give a first crop of compound 12 (114.7 g).

The isolated yield was lower than expected. Hence, the mother liquor and the AcOH washing liquid were combined and concentrated and the resulting residue (volume 4 L) was allowed to cool to room temperature (22° C.) overnight. The suspension was filtered and the filter cake was washed with acetic acid (200 ml) and water (2×1 L). The yellow filter cake was dried in a vacuum oven at 60° C. (2 mbar) for 6 hours to give a second crop of compound 12 (23.3 g).

As the recovery was still low, the wet material from the initial filtration over the polypropylene filter (ca. 410 g, including charcoal) was transferred back to the reaction vessel and was stirred with acetic acid (12 L) at 120-125° C. for 2 hours, after which time the temperature was lowered to 95° C. to enable filtration. The residue on the filter was washed with 2 L of hot acetic acid and the combined filtrates were cooled to 24° C. overnight. The resulting suspension was filtered, the filter cake was washed with acetic acid (0.5 L) and water (3×1 L). The white solid was dried in a rotary evaporator at 60° C. at 6 mbar for 6 hours to give a third crop of compound 12 (95.1 g). An acetic acid rinse of the charcoal (2 L) was filtered separately and washed with acetic acid (100 ml) and water (1 L). The white solid was dried in a vacuum oven at 60° C. (2 mbar) for 6 hours to give a fourth crop of compound 12 (5.4 g).

The wet charcoal residue (79 g) was treated one more time with 5 L acetic acid at 120-125° C. for 2 hours. After cooling to 95° C. and filtration, the charcoal residue was washed with 1 L acetic acid. The combined filtrate was evaporated to volume of ca. 1 L, cooled down to 22° C., filtered and washed with acetic acid (1×200 ml) and water (2×250 ml). The resulting white solid was dried in a vacuum oven at 60° C. and 2 mbar for 6 hours to give a fifth crop of compound 12 (11.6 g; MAKA08-039-5). The mother liquors after the precipitation of third and fourth crops were combined, concentrated to a volume of 700 ml, allowed to cool down to 22° C. and then filtered. The resulting solid was washed with acetic acid (1×100 ml) and water (2×250 ml) and dried in a vacuum oven at 60° C. and 2 mbar for 6 hours to give a sixth crop of compound 12 (17.5 g).

The six crops of compound 12 were each individually analyzed by LCMS and the analyses revealed that the product batches contained only little impurities, except for the impurity eluting at 24.3 minutes, which was present in all crops at levels of 2.6% to 3.3% (see Table 2).

TABLE 2

The isolated crops of final product Compound 12.

| Crop No.: | Amount [g] | Purity [%] | Impurity RT 24.3 [%] |
|---|---|---|---|
| 1 | 114.7* | 96.6 | 2.93 |
| 2 | 95.1 | 96.8 | 2.64 |
| 3 | 5.4 | 97.1 | 2.61 |
| 4 | 23.3 | 95.6 | 3.17 |
| 5 | 17.5 | 95.2 | 3.29 |
| 6 | 11.6 | 92.3 | 7.20 |

*(available 111.4 g)

Purification of Compound 12

Batches of compound 12 containing less than 3.5% of IMP 24.3 were combined and purified by re-slurrying in toluene. The suspension of compound 12 (278.24 g, 728 mmol) in toluene (13.5 l) was heated to reflux under stirring and refluxed for 2 hours. The suspension was cooled to 30° C. over a period of 80 minutes and filtered (sintered glass filter S2). The filter cake was washed with toluene (5.2 l) (in three portions 2.2 l, 1.5 l, 1.5 l) and dried in a hot air dryer at 70° C. for 14 hours to give purified compound 12 (268.4 g, 702 mmol, 96% yield, 98.7% purity). The content of acetic acid was estimated from $^1$H NMR spectrum to be 1.6% (w/w).

The prepared material was also tested for the content of selected metals (Pd, Cu, Zn). As shown in Table 3 the amounts of residual metals was well below <10 ppm (ICH guidelines).

TABLE 3

The content of selected metals in compound 12 (ICP-MS).

| Metal | Concentration |
|---|---|
| Cu | 0.35 |
| Pd | 3.2 |
| Zn | <0.5 |

The invention, therefore, is also directed to compounds of Formula (I), or pharmaceutically acceptable salts thereof, including 9-benzyl-2-(4-methylphenyl)-2,6-dihydro[1,2,4]triazolo[4,3-c]quinazoline-3,5-dione, prepared by the processes described in Schemes 1 or 2.

The compounds of Formula (I), or pharmaceutically acceptable salts thereof, prepared by the processes described herein, may be formulated into conventional pharmaceutical compositions comprising a compound of Formula (I), or a pharmaceutically acceptable salt thereof, prepared by the processes described herein, in association with a pharmaceutically acceptable carrier or excipient. Preferably, the pharmaceutical composition of the invention comprises 9-benzyl-2-(4-methylphenyl)-2,6-dihydro[1,2,4]triazolo[4,3-c]quinazoline-3,5-dione, prepared by the process described herein. The pharmaceutically acceptable carriers can be either solid or liquid. Solid form preparations include, but are not limited to, powders, tablets, dispersible granules, capsules, cachets, and suppositories.

A solid carrier can be at least one substance, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component, in tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term "composition" is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain at least one coloring, sweetening, flavoring, and/or preservative agents.

Depending on the mode of administration, the pharmaceutical composition will include from about 0.05% w/w to about 99% w, more particularly, from about 0.10% w to 50% w, of a compound of Formula (I), all percentages by weight being based on the total weight of the composition. One skilled in the art can determine a therapeutically effective amount for the practice of the invention using known criteria including the age, weight, and response of the individual patient, and interpreted within the context of the disease which is being treated or which is being prevented.

The compounds of Formula (I), or pharmaceutically acceptable salts thereof, prepared by the processes described herein, and the pharmaceutical compositions thereof, may be used to treat anxiolytic, anticonvulsant, sedative-hypnotic, and myorelaxant conditions, as well as anxiogenic, somnolytic, and convulsant conditions. Therefore, the invention is also related to a method for treating anxiolytic, anticonvulsant, sedative-hypnotic, and myorelaxant conditions, as well as anxiogenic, somnolytic, and convulsant conditions in mammals, including humans, by administering a therapeutically effective amount of at least one of the compounds of Formula (I), prepared by the processes described herein, or by administering a therapeutically effective amount of at least one pharmaceutical composition thereof.

Preferably, the invention relates to a method for treating anxiolytic, anticonvulsant, sedative-hypnotic, and myorelaxant conditions, as well as anxiogenic, somnolytic, and convulsant conditions in mammals, including humans, by administering a therapeutically effective amount of 9-benzyl-2-(4-methylphenyl)-2,6-dihydro[1,2,4]triazolo[4,3-c]quinazoline-3,5-dione, prepared by the process described herein, or by administering a therapeutically effective amount of at least one pharmaceutical composition thereof.

The claimed invention is:

1. A process for preparing a compound of Formula (I):

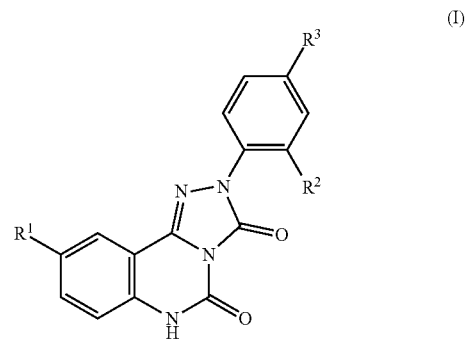

wherein:
  $R^1$ is halogen, $C_{1-2}$ alkyl, $CF_3$, $C_{1-3}$ alkyl-C(O)OH, $C_{1-3}$ alkyl-phenyl, $C_{1-2}$ alkyl-pyridyl, $C_{2-3}$ alkenyl-phenyl, or $C_{2-3}$ alkynyl-phenyl;
  $R^2$ is hydrogen or halogen; and
  $R^3$ is hydrogen, halogen, or $C_{1-2}$ alkyl;
wherein the process comprises the following steps:
1) reacting a compound of Formula (II):

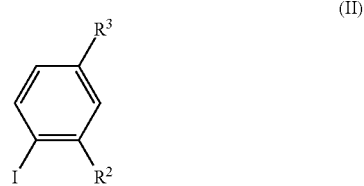

wherein:
  $R^2$ is hydrogen or halogen; and
  $R^3$ is hydrogen, halogen, or $C_{1-2}$ alkyl;
with a compound of Formula (III):

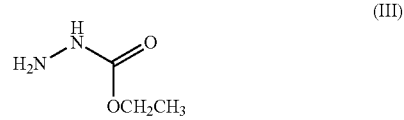

in the presence of cesium carbonate, copper(I) iodide, and dimethylsulfoxide, to form a compound of Formula (IV):

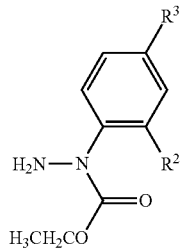

wherein:
 $R^2$ is hydrogen or halogen; and
 $R^3$ is hydrogen, halogen, or $C_{1-2}$ alkyl;

2) reacting a compound of Formula (V):

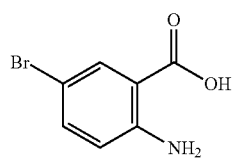

with a compound of the following formula:

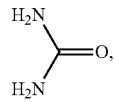

to form a compound of Formula (VI):

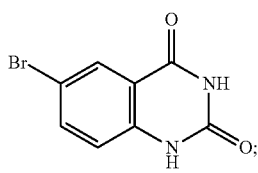

3) reacting the compound of Formula (VI) above with a compound of Formula (XI):

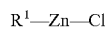 (XI)

wherein:
 $R^1$ is halogen, $C_{1-2}$ alkyl, $CF_3$, $C_{1-3}$ alkyl-C(O)OH, $C_{1-3}$ alkyl-phenyl, $C_{1-2}$ alkyl-pyridyl, $C_{2-3}$ alkenyl-phenyl, or $C_{2-3}$ alkynyl-phenyl;

in the presence of palladium(II) acetate and tri-tert-butylphosphonium tetrafluoroborate, to form a compound of Formula (VII):

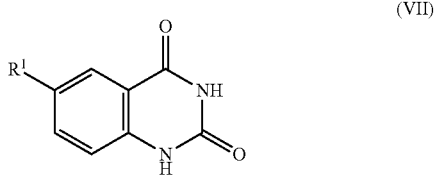

wherein:
 $R^1$ is halogen, $C_{1-2}$ alkyl, $CF_3$, $C_{1-3}$ alkyl-C(O)OH, $C_{1-3}$ alkyl-phenyl, $C_{1-2}$ alkyl-pyridyl, $C_{2-3}$ alkenyl-phenyl, or $C_{2-3}$ alkynyl-phenyl;

4) reacting the compound of Formula (VII) above with a compound of the following formula:

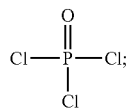

in the presence of N,N-diisopropylethylamine, to form a compound of Formula (VIII):

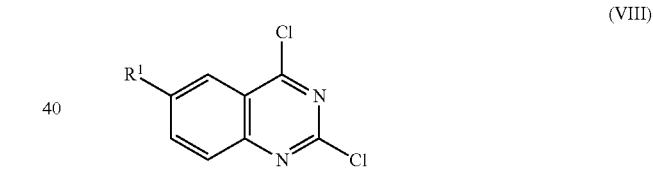

wherein:
 $R^1$ is halogen, $C_{1-2}$ alkyl, $CF_3$, $C_{1-3}$ alkyl-C(O)OH, $C_{1-3}$ alkyl-phenyl, $C_{1-2}$ alkyl-pyridyl, $C_{2-3}$ alkenyl-phenyl, or $C_{2-3}$ alkynyl-phenyl;

5) reacting the compound of Formula (VIII) above with the compound of Formula (IV):

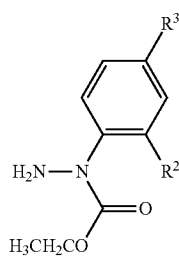

wherein:

R² is hydrogen or halogen; and

R³ is hydrogen, halogen, or C₁₋₂ alkyl;

in the presence of N,N-diisopropylethylamine, to form a compound of Formula (IX):

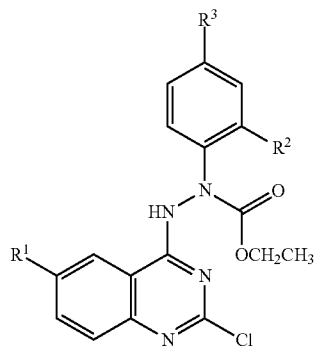

(IX)

wherein:

R¹ is halogen, C₁₋₂ alkyl, CF₃, C₁₋₃ alkyl-C(O)OH, C₁₋₃ alkyl-phenyl, C₁₋₂ alkyl-pyridyl, C₂₋₃ alkenyl-phenyl, or C₂₋₃ alkynyl-phenyl;

R² is hydrogen or halogen; and

R³ is hydrogen, halogen, or C₁₋₂ alkyl;

6) reacting the compound of Formula (IX) above with sodium hydroxide, to form a compound of Formula (X):

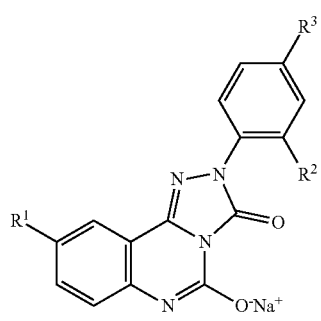

(X)

wherein:

R¹ is halogen, C₁₋₂ alkyl, CF₃, C₁₋₃ alkyl-C(O)OH, C₁₋₃ alkyl-phenyl, C₁₋₂ alkyl-pyridyl, C₂₋₃ alkenyl-phenyl, or C₂₋₃ alkynyl-phenyl;

R² is hydrogen or halogen; and

R³ is hydrogen, halogen, or C₁₋₂ alkyl; and 7) reacting the compound of Formula (X) above with acetic acid, to form the compound of Formula (I) above.

2. The process of claim 1, wherein the compound of Formula (I) is a compound of Formula 12:

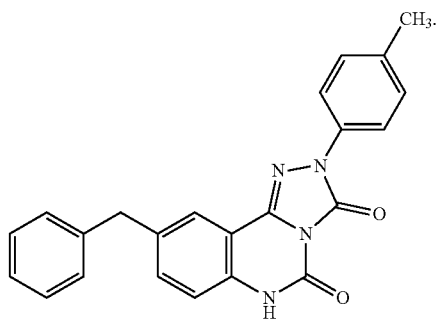

12

3. A process for preparing a compound of Formula 12:

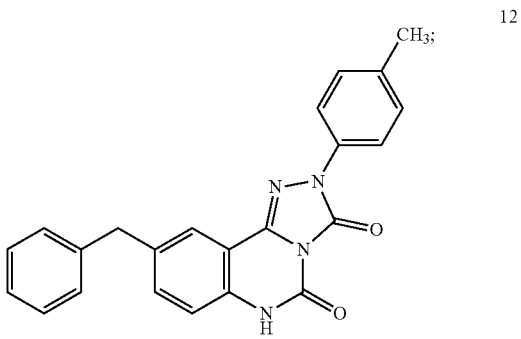 [SMILES: Cc1ccc(-n2nc3c4cc(Cc5ccccc5)ccc4[nH]c(=O)n3c2=O)cc1]

12 wherein the process comprises the following steps:

1) reacting a compound of Formula 1:

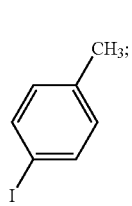

1 with a compound of Formula 2:

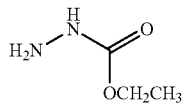

in the presence of cesium carbonate, copper(I) iodide, and dimethylsulfoxide, to form a compound of Formula 4:

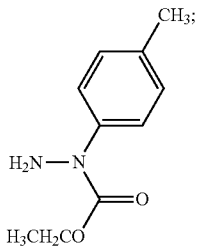

2) reacting a compound of Formula 5:

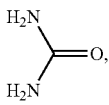

with a compound of the following formula:

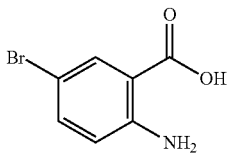

to form a compound of Formula 6:

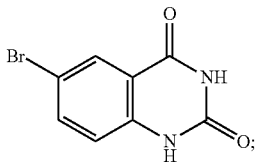

3) reacting the compound of Formula 6 above with a compound of Formula 13:

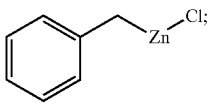

in the presence of palladium(II) acetate and tri-tert-butylphosphonium tetrafluoroborate, to form a compound of Formula 8:

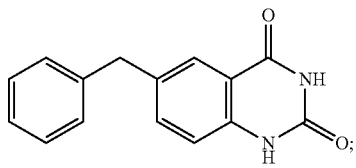

4) reacting the compound of Formula 8 above with a compound of the following formula:

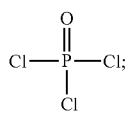

in the presence of N,N-diisopropylethylamine, to form a compound of Formula 9:

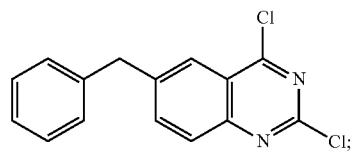

5) reacting the compound of formula 9 above with the compound of Formula 4:

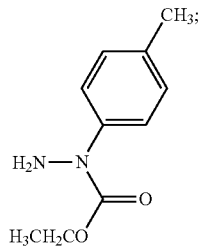

in the presence of N,N-diisopropylethylamine, to form a compound of Formula 10:

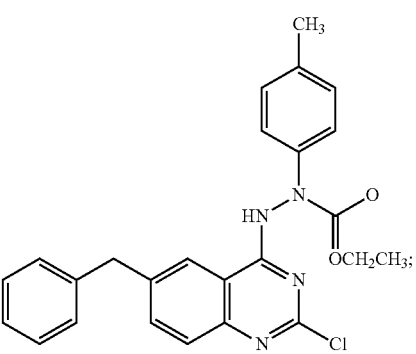

6) reacting the compound of Formula 10 above with sodium hydroxide, to form a compound of Formula 11:
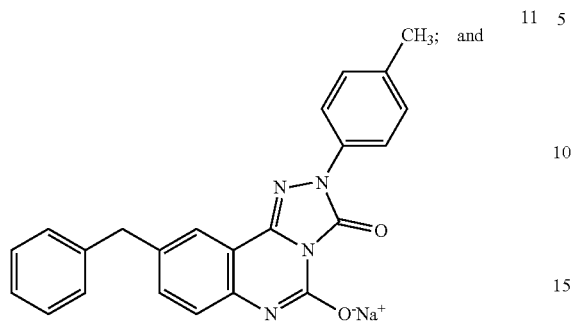
7) reacting the compound of Formula 11 above with acetic acid, to form the compound of Formula 12 above.
* * * * *